(12) United States Patent
Grubac et al.

(10) Patent No.: US 9,283,381 B2
(45) Date of Patent: Mar. 15, 2016

(54) FIXATION FOR IMPLANTABLE MEDICAL DEVICES

(71) Applicant: Medtronic, Inc., Minneapolis, MN (US)

(72) Inventors: Vladimir Grubac, Brooklyn Park, MN (US); Jonathan L Kuhn, Ham Lake, MN (US); Kenneth D Rys, Minneapolis, MN (US); Richard W Swenson, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/854,964

(22) Filed: Sep. 15, 2015

(65) Prior Publication Data
US 2016/0001068 A1    Jan. 7, 2016

Related U.S. Application Data

(62) Division of application No. 13/955,674, filed on Jul. 31, 2013, now Pat. No. 9,155,882.

(51) Int. Cl.
*A61N 1/05* (2006.01)
*A61N 1/362* (2006.01)

(52) U.S. Cl.
CPC .............. *A61N 1/0573* (2013.01); *A61N 1/362* (2013.01)

(58) Field of Classification Search
CPC ..... A61N 1/057; A61N 1/0573; A61N 1/059; A61N 1/362
USPC .......................................... 607/126, 128, 130
See application file for complete search history.

(56) References Cited

U.S. PATENT DOCUMENTS

| 3,814,104 A | 6/1974 | Irnich et al. |
| 4,103,690 A | 8/1978 | Harris |
| 5,492,119 A | 2/1996 | Abrams |
| 6,684,109 B1 | 1/2004 | Osypka |

(Continued)

FOREIGN PATENT DOCUMENTS

| EP | 0 212 955 A2 | 3/1987 |
| WO | 95/20993 | 8/1995 |

(Continued)

OTHER PUBLICATIONS (PCT/US2014/047442) PCT Notification of Transmittal of the International Search Report and the Written Opinion of the International Searching Authority.

(Continued)

*Primary Examiner* — Paula J Stice
(74) *Attorney, Agent, or Firm* — Evans M. Mburu

(57) ABSTRACT

A tine portion of an implantable medical device includes a hook segment and a distal segment extending therefrom, wherein the hook segment is pre-set to extend along a curvature and is elastically deformable therefrom to an open position. The distal segment includes a tooth and an end that surrounds the tooth, wherein the end includes a pair of legs and a distal arch. The legs extend along a length of, and on opposing sides of the tooth, and the distal arch extends between the legs, distal to a tissue-piercing tip of the tooth. When the hook segment is in the open position, and a force is applied along a longitudinal axis of the device, to push the distal arch of the distal segment against tissue, for initial tissue penetration, the legs of the end of the distal segment bend in elastic deformation to expose the tissue-piercing tip to the tissue.

11 Claims, 19 Drawing Sheets

(56) References Cited

U.S. PATENT DOCUMENTS

| | | |
|---|---|---|
| 7,149,587 B2 | 12/2006 | Wardle et al. |
| 7,509,169 B2 | 3/2009 | Eigler et al. |
| 8,452,420 B2 | 5/2013 | Flach et al. |
| 2006/0247753 A1 | 11/2006 | Wenger et al. |
| 2011/0251660 A1 | 10/2011 | Griswold |
| 2011/0251662 A1 | 10/2011 | Griswold et al. |
| 2012/0108986 A1 | 5/2012 | Beasley et al. |
| 2012/0116489 A1 | 5/2012 | Khairkhahan et al. |
| 2012/0172690 A1 | 7/2012 | Anderson et al. |
| 2012/0172892 A1 | 7/2012 | Grubac et al. |
| 2012/0232565 A1 | 9/2012 | Kveen et al. |

FOREIGN PATENT DOCUMENTS

| | | |
|---|---|---|
| WO | 01/02053 A1 | 1/2001 |
| WO | 2012135530 A1 | 10/2012 |

OTHER PUBLICATIONS (PCT/US2014/047962) PCT Notification of Transmittal of the International Search Report and the Written Opinion of the International Searching Authority.

(PCT/US2014/048264) PCT Notification of Transmittal of the International Search Report and the Written Opinion of the International Searching Authority.

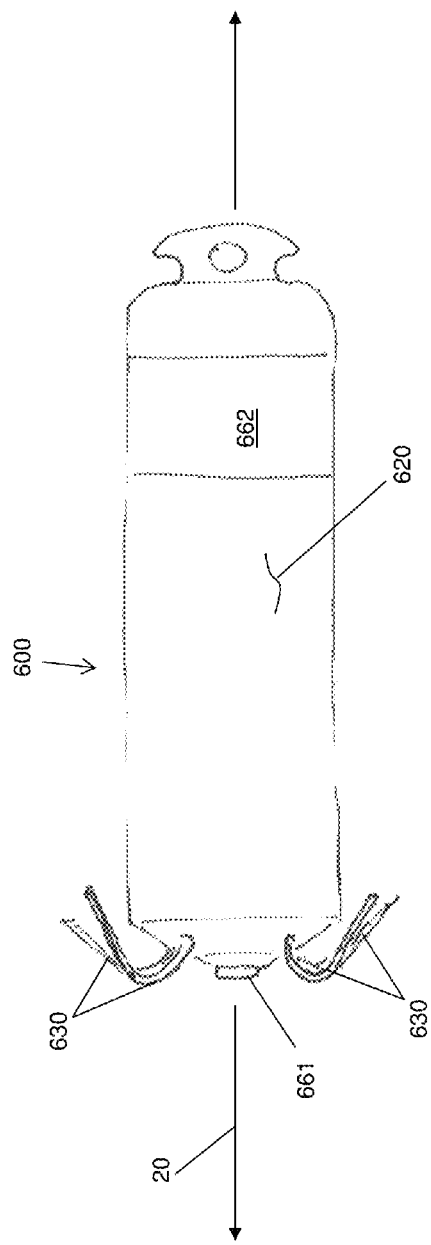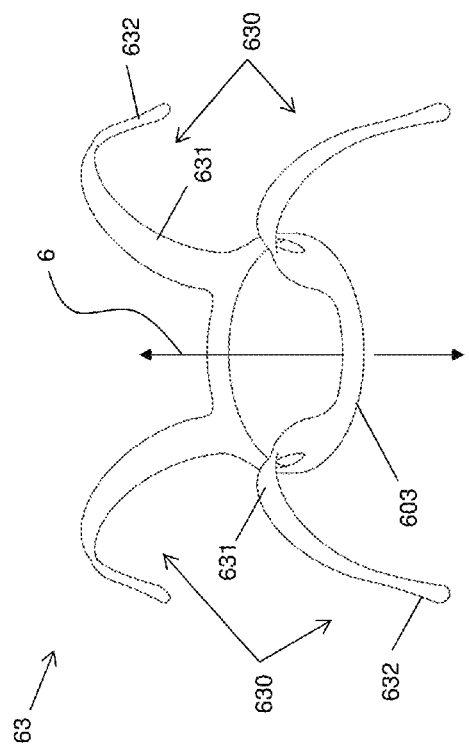
FIGURE 6A
FIGURE 6B

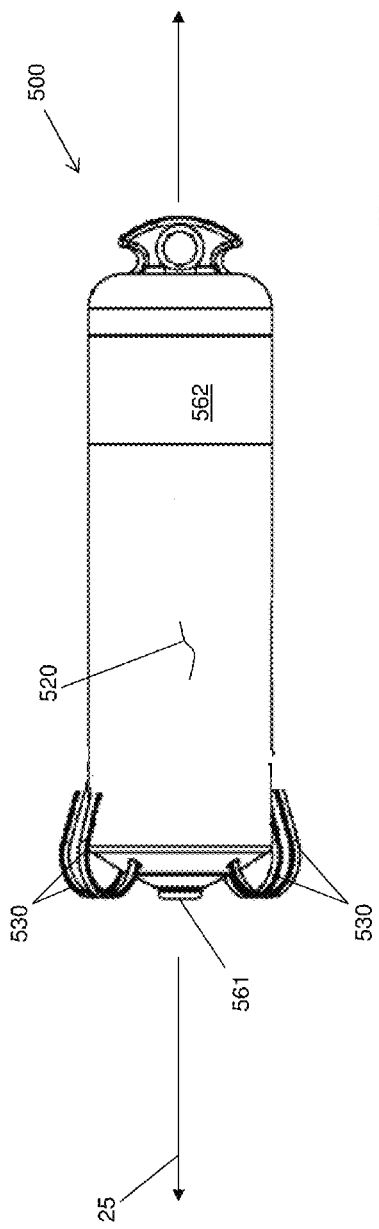
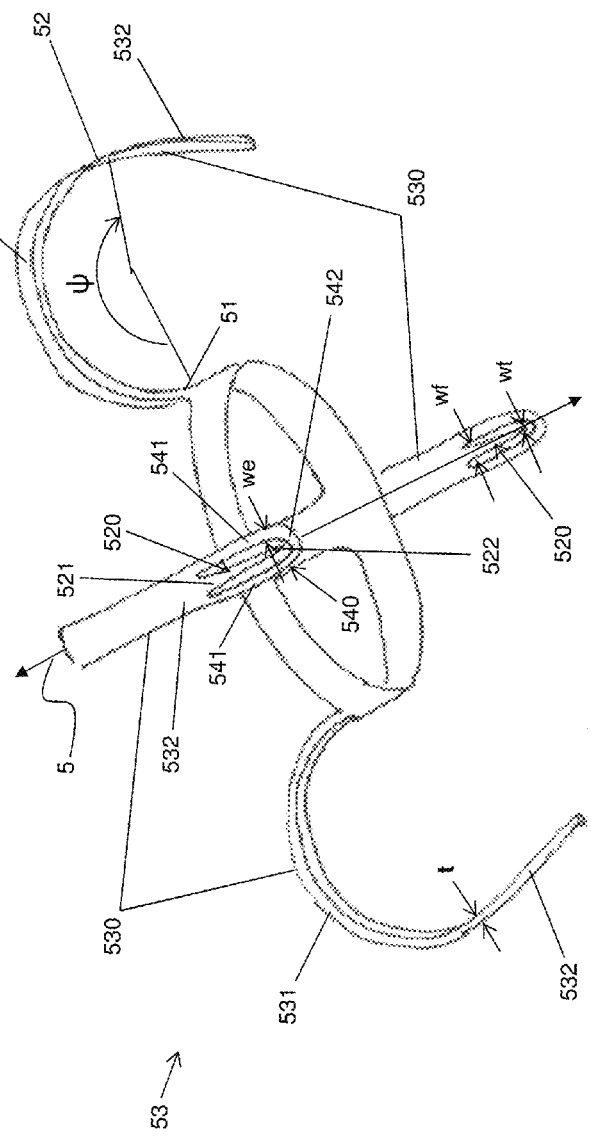
FIGURE 10A
FIGURE 10B

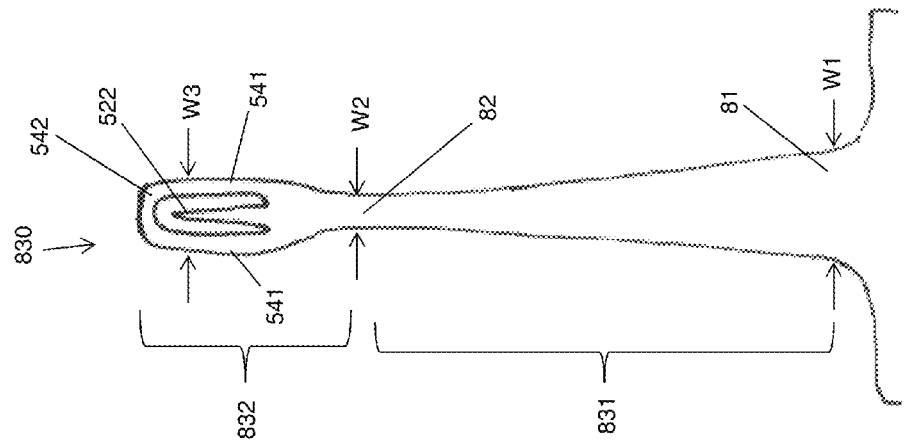
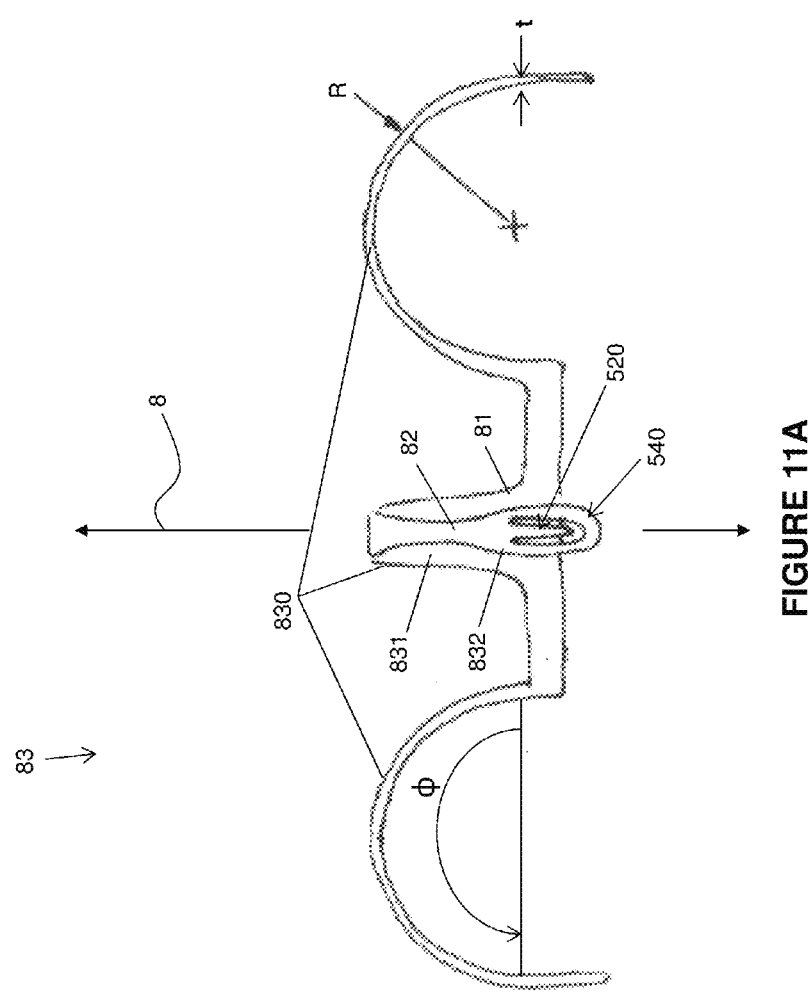
FIGURE 11A
FIGURE 11B

FIXATION FOR IMPLANTABLE MEDICAL DEVICES

CROSS-REFERENCE TO RELATED APPLICATION

The present application claims priority to U.S. patent application Ser. No. 13/955,674 filed Jul. 31, 2013, now issued as U.S. Pat. No. 9,155,882, which is herein incorporated by reference in its entirety. The present application is also related to the commonly-assigned co-pending U.S. patent application Ser. No. 13/955,393, filed on Jul. 31, 2013 and U.S. patent application Ser. No. 13/955,127, filed on Jul. 31, 2013, now issued as U.S. Pat. No. 9,119,959, which are herein incorporated by reference, in their entirety.

TECHNICAL FIELD

The present invention pertains to implantable medical devices, and, more specifically, to tissue-penetrating fixation components thereof.

BACKGROUND

An implantable medical device, for the delivery of stimulation therapy and/or for diagnostic sensing, may include at least one tissue-penetrating fixation component configured to hold the device at an implant location. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. FIG. 2 is a plan view of an exemplary implantable medical device 200, which includes a tissue-penetrating fixation component formed by a plurality of tine portions 230. FIG. 2 further illustrates device 200 including a hermitically sealed housing 220 that contains control electronics and a power source (not shown), and which defines a longitudinal axis 2 of device 200. Housing 220 may be formed from a medical grade stainless steel or titanium alloy and have an insulative layer formed thereover, for example, parylene, polyimide, or urethane. With further reference to FIG. 2, device 200 includes a pair of electrodes 261, 262, which may form a bipolar pair for cardiac pacing and sensing; tine portions 230 surround electrode 261 and are configured to penetrate tissue in order to hold electrode 261 in intimate contact with tissue, for example, at one of the aforementioned implant sites, while securing, or fixating device 200 for chronic implantation at the site. Further description of a suitable construction for device 200 may be found in the co-pending and commonly assigned United States Patent Application having the pre-grant publication number 2012/0172690 A1.

With reference to FIG. 3A, device 200 may be delivered to an implant location via a delivery catheter 300. For example, with reference to FIG. 1, if the target implant site is located in the right atrium RA, coronary vein CV, or right ventricle RV, a distal end 310 of catheter 300 may be maneuvered into the heart through a superior vena cava SVC or an inferior vena cava IVC, according to a transveous delivery method known in the art. FIG. 3A shows a partial cross-section of distal end 310 of catheter 300, which is formed like a cup to hold and contain device 200 for delivery to the implant site. FIG. 3A illustrates device 200 having been loaded into distal end 310 so that a hook segment 231 of each tine portion 230 is elastically deformed, from a pre-set curvature thereof, to an open position, at which a distal segment 232 of each tine portion 230 extends distally toward an opening 313 of catheter distal end 310. Each tine portion 230 is preferably formed from a superelastic material, such as Nitinol. FIG. 3A further illustrates a deployment element 320 abutting a proximal end of device 200 and extending proximally therefrom, through a lumen of catheter 300, and out from a proximal opening 301 thereof. Element 320 may be moved, per arrow M, by an operator to push device 200, per arrow P, out from opening 313 of distal end 310, for example, when opening 313 has been located by the operator in close proximity to tissue at the target implant site.

FIG. 3B, is an enlarged view of distal segment 232 of one of tine portions 230, wherein a tissue-piercing tip 322, which terminates distal segment 232, has just been pushed out through opening 313 of distal end 310 of catheter 300 and into contact with tissue T. FIG. 3B illustrates distal segment 232 supported by the surrounding wall of distal end 310, in proximity to opening 313, so that the push force of deployment element 320 is effectively transferred through tip 322 to first compress the tissue T, as shown, and then to pierce the tissue T for penetration therein, which is shown in FIGS. 3C-D. FIGS. 3C-D illustrate partial tine penetration and full tine penetration, respectively, as deployment element 320 continues to push device 200 out opening 313. It can be seen that the elastic nature of each tine portion 230, once the constraint of the distal end 310 is withdrawn, allows the corresponding hook segment 231 to relax back toward the pre-set curvature thereof within the tissue. The full penetration of tine portions 230, shown FIG. 3D, is representative of acute fixation of device 200 at the implant site, for example, for the evaluation of device performance (e.g., pacing and sensing via electrodes 261, 262). It should be noted that, at some implant sites, tine portions 230 may, at full penetration, extend back out from tissue T, for example, generally toward distal end 310 of catheter 300.

With further reference to FIG. 3D, a tether 350 is shown looping through an eye feature 205 formed at the proximal end of device 200; tether 350 extends proximally through a lumen of deployment element 320 to a proximal end 351 thereof, outside a proximal end of deployment element 320, which may be seen in FIG. 3A. Thus, if the performance of acutely fixated device 200 is unsatisfactory, the operator may use tether 350 to pull device 200 back into distal end 310, thereby withdrawing tine portions 230 from the tissue, so that device may be moved by delivery catheter 300 to another potential implant site. Alternately, if the acutely fixated device 200 performs satisfactorily, proximal end 351 of tether 350 may be severed to pull tether 350 out from eye feature 205 of device 200, and the fully penetrated tine portions 230 continue to fixate device 200 for chronic implant.

The aforementioned co-pending and commonly assigned United States Patent Application '690 discloses suitable embodiments of a fixation component having tine portions similar to tine portions 230, wherein the tine portions exhibit a suitable baseline performance, for example, in terms of a deployment force, an acute retraction force (for repositioning), atraumatic retraction, and acute and chronic fixation forces. Yet, there is still a need for new configurations of tine portions for implantable devices, like device 200, that may further enhance fixation.

SUMMARY

Embodiments of the present invention encompass implantable medical devices (e.g., cardiac pacemakers) and tissue-penetrating fixation components thereof, which include one or more tine portions that are configured to mitigate the risk of compressing, for example, to the point of occlusion, blood vessels in proximity to the implant site, and to reduce the risk of tissue trauma during the retraction thereof from the tissue, for example, for repositioning. In certain embodiments, the tine portions may also be configured for increased strain relief during the flexing thereof, either at initial implant (particularly in cases where the retraction of penetrated tines is necessary for repositioning the device), or when subject to cyclic loading during a chronic implant of the fixated device, for example, within a beating heart.

According to some embodiments, a tine portion of a tissue-penetrating component of an implantable medical device includes a hook segment and a relatively short distal segment, wherein the distal segment includes a tooth and an end that surrounds the tooth. The hook segment is elastically deformable from a pre-set curvature thereof to an open position, and the distal segment is pre-set to extend from a distal end of the hook segment along a relatively straight line that is approximately tangent to the distal end. The end of the distal segment includes a pair of legs and a distal arch, wherein the legs extend along a length of the tooth, on opposing sides thereof, and the distal arch extends between the legs and distal to a tissue-piercing tip of the tooth. The legs of the end are configured to bend in elastic deformation, when the hook segment is elastically deformed to the open position and a force is applied to push the distal arch of the distal segment against tissue, for initial tissue penetration, so that the bending of the legs expose the tip of the tooth to the tissue.

The tissue-penetrating component, according to some embodiments, further includes a base portion, for example, in the form of a ring, that is configured to be fixedly attached to the implantable medical device, wherein the tine portion may be one of a plurality of tine portions integrally formed with the base portion. According to some preferred embodiments, each tine portion has a substantially constant thickness along an entire length thereof, from a proximal end of the hook segment to the distal arch of the end of the distal segment. Strain relief of each tine portion may be provided by a tapering of the hook segment thereof, from a first width thereof, in proximity to the proximal end thereof, to a second, smaller width thereof, in proximity to a distal end thereof. And, in some of the tapering embodiments, a width of distal segment, defined by the pair of legs thereof, is greater than the second width of the hook segment.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 6A is a plan view of an implantable medical device, according to some embodiments of the present invention;

FIG. 6B is a perspective view of a tissue-penetrating fixation component, according to some embodiments of the present invention, separated from the device of FIG. 6A;

FIG. 10A is a plan view of an implantable medical device, according to some alternate embodiments of the present invention;

FIG. 10B is a perspective view of a tissue-penetrating fixation component, according to some embodiments, separated from the device of FIG. 10A;

FIG. 11A is an elevation view of a tissue-penetrating fixation component, according to yet further embodiments of the present invention, which may be incorporated in the exemplary device of FIG. 10A; and FIG. 11B is a plan view of a tine portion of the component of FIG. 11A, according to some embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 3A:
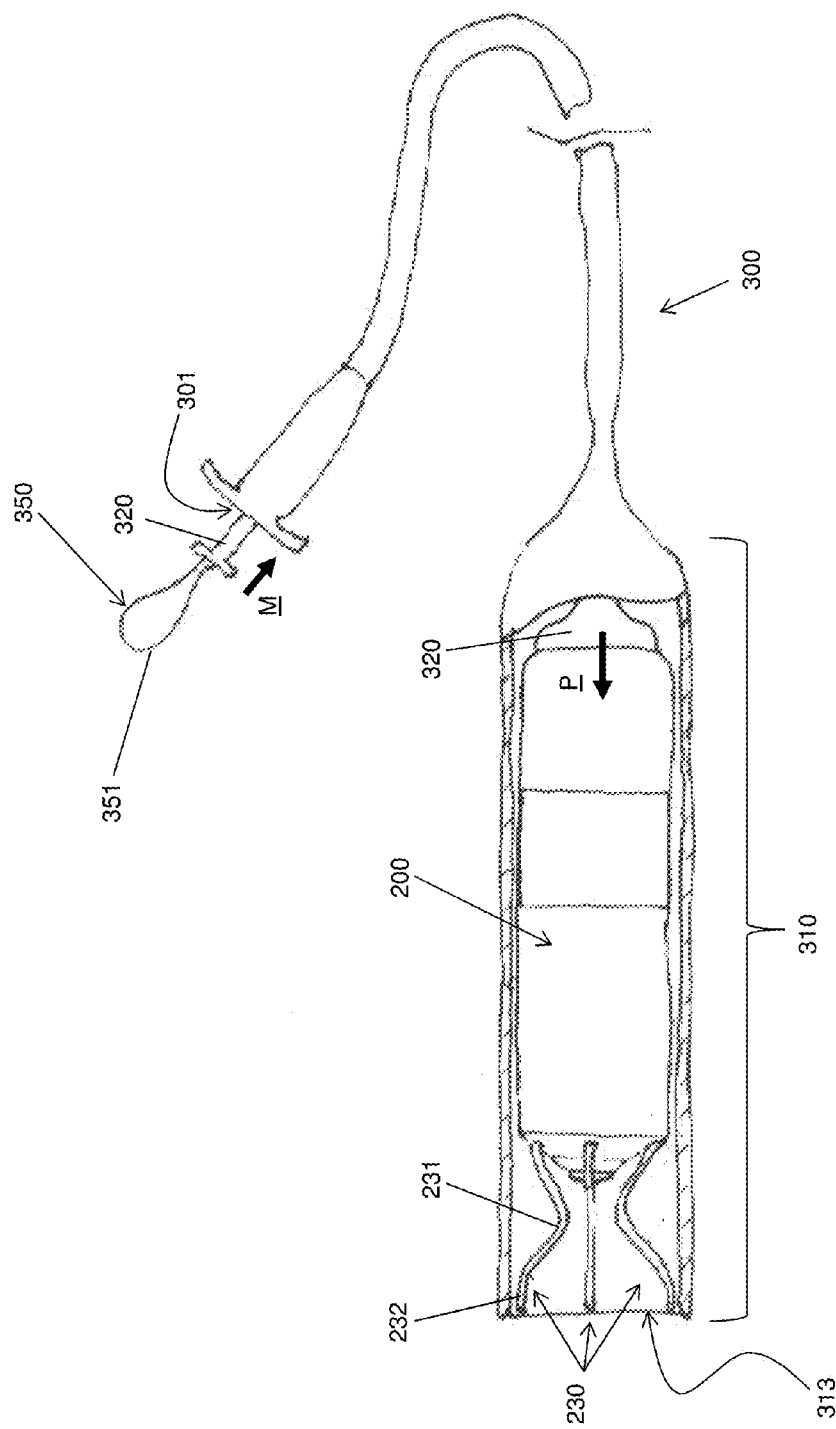
FIG. 3A is a plan view of the medical device loaded in a delivery catheter, according to some embodiments, wherein tine portions of a tissue-penetrating fixation component thereof are elastically deformed into an open position.
Figure 3B:
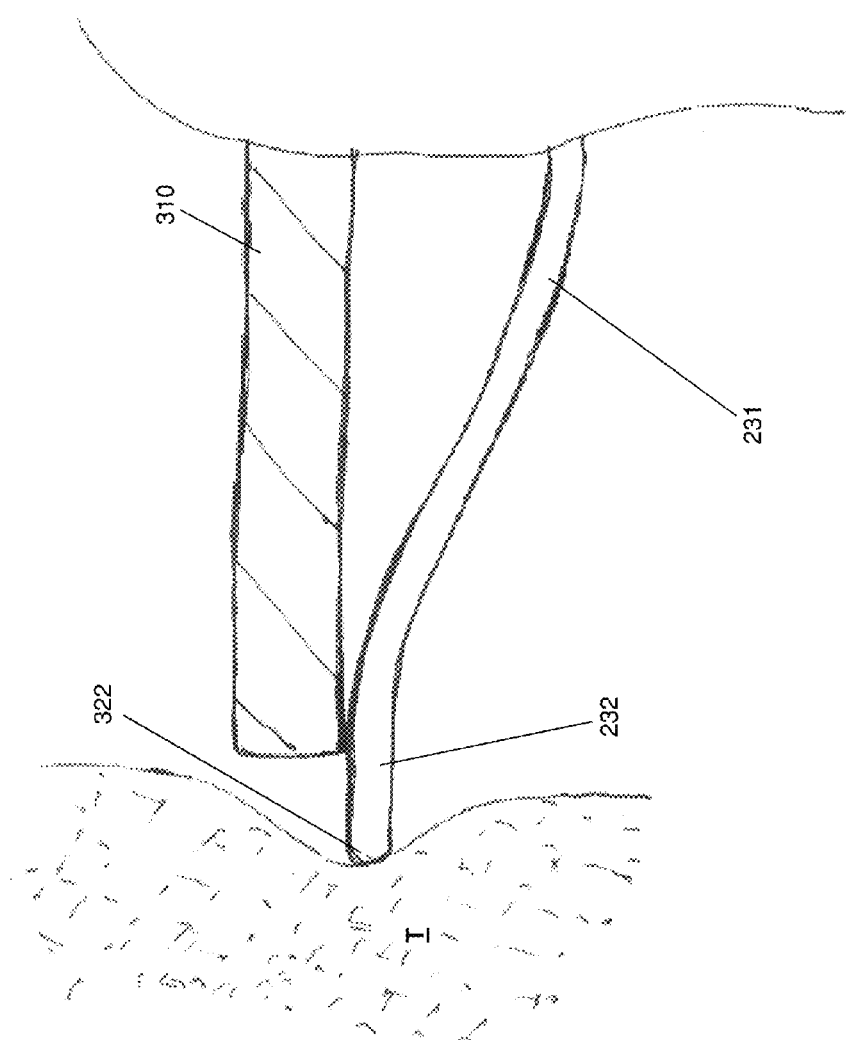
FIG. 3B is an enlarged detail view of one of the tine portions initially contacting tissue at an implant site.
Figure 3C:
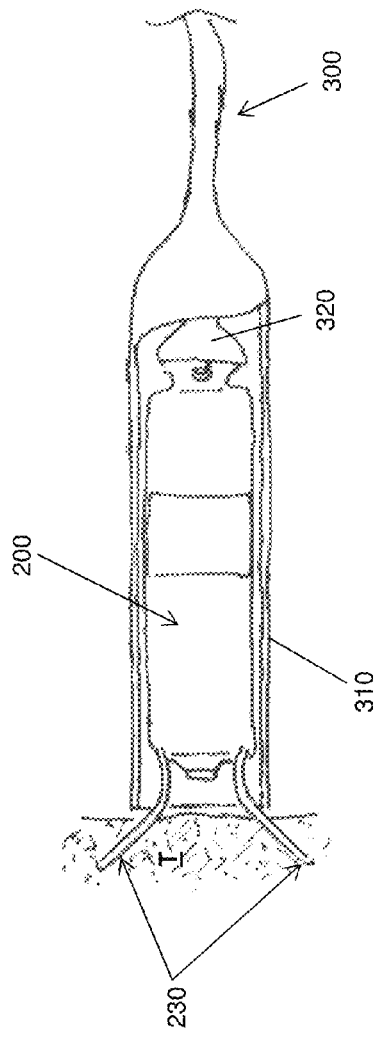
FIGS. 3C-D are plan views of the device and catheter in subsequent steps of implanting the device, when the tine portions have penetrated the tissue.
Figure 3D:
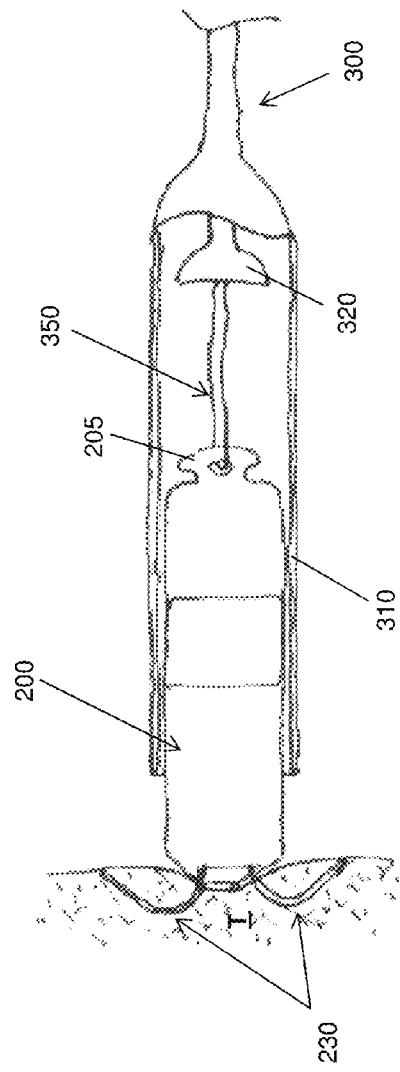
Figure 4B:
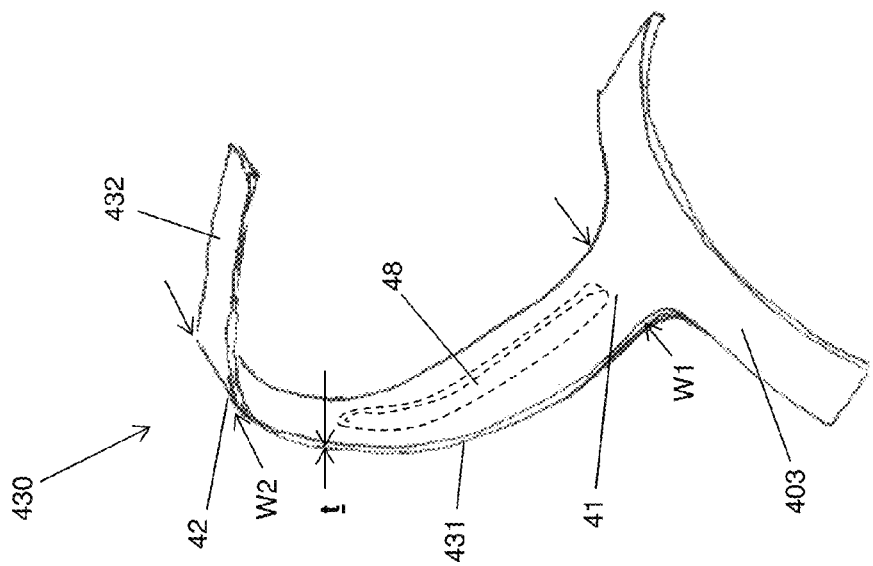
FIG. 4B is a perspective view of a tapered tine portion, according to some embodiments of the present invention.
Figure 4A:
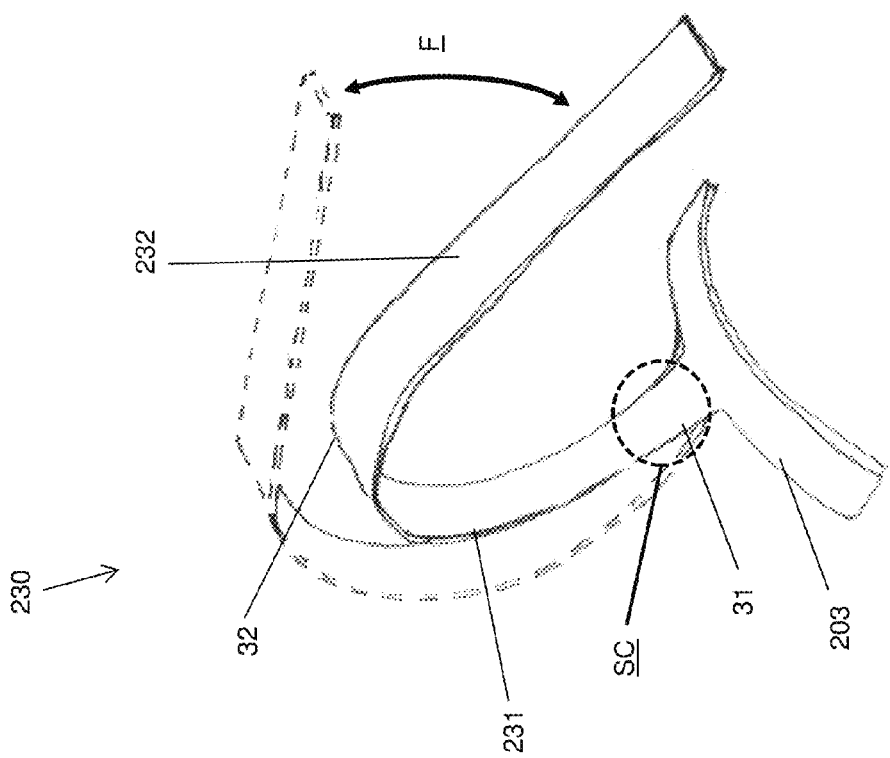
FIG. 4A is a schematic representation of a flexing tine portion.

FIG. 4A is a schematic representation of one of tine portions 230 isolated from the above-described implantable medical device 200, wherein an exemplary flexing, per arrow F, of tine portion 230 is illustrated. Such flexing may be encountered by tine portion 230, once tine portion 230 has penetrated tissue to fix device 200 at a chronic implant site for cardiac monitoring and/or therapy, for example, as illustrated in FIG. 3D. Thus, fatigue life is a consideration influencing the configuration of tine portions for those implantable medical devices that may be subjected to cyclic loading caused by hundreds of millions of heart beats, over the life of their implant. In FIG. 4A, a zone of stress concentration SC, for example, in response to the flexing per arrow F, is circled; zone SC is located in proximity to a proximal end 31 of hook segment 231 of tine portion 230, where hook segment 231 joins with a base portion 203. Base portion 203 and tine portion 230 may be integrally formed, wherein base portion 203 is configured to be fixedly attached to device 200. Stress concentration in zone SC may also result from deformation of hook segment 231 into the open position (FIG. 3A), for example, upon initial loading of device 200 and retraction of device 200 back into distal end 310 of catheter for repositioning, which, in combination with the repeated force of deployment, can potentially push tine portion 230 toward an elastic limit and may make tine portion 230 subsequently more vulnerable to fatigue under the aforementioned cyclic loading. Although rounded edges of tine portions 230 effectively reduce the concentration of stress, as previously described in the aforementioned commonly-assigned United States Patent Application '690, some embodiments of the present invention incorporate tine portions that have tapered hook segments to further address the stress concentration, for example, as illustrated in FIG. 4B.

FIG. 4B is a perspective view of a tine portion 430, according to some embodiments, one or more of which may be integrated into device 200, as substitute for tine portions 230. A base portion 403 is shown integrally formed with tine portion 430, according to some preferred embodiments, wherein base portion 403 is configured for attachment to a medical device, such as device 200. FIG. 4B illustrates a hook segment 431 of tine portion 430 extending from a first end 41 thereof, in proximity to base portion 403, to a second end 42 thereof, in proximity to a distal segment 432 of tine portion 430, wherein hook segment 431 tapers from a first width W1, in proximity to proximal end 41, to a smaller, second width W2, in proximity to a distal end 42 of hook segment 431. The tapering of hook segment 431 provides strain relief during the aforementioned deformation/flexing, to alleviate the aforementioned stress concentration. FIG. 4B further illustrates an optional slot 48 (dashed lines), which may be formed through a thickness t of tine portion 430, and extend between first width W1 and second width W2. The inclusion of slot 48 provides an additional means for providing strain relief, for example, when a limit on how narrow second width W2 may be, for example, no smaller than approximately 0.020-0.025 inch, so that distal segment 432 does not tear tissue upon retraction therefrom. According to some embodiments, optional slot 48 may include internal shear tabs (not shown) to help distribute out of plane loads, for example, orthogonal to the illustrated direction of flexing, per arrow F of FIG. 4A.

With further reference to FIGS. 4A-B, distal segment 432 of tine portion 430 is shown having a shorter length than distal segment 232 of tine portion 230, for example, to provide more flexibility in selecting a suitable implant site without risking undue trauma to tissue, upon penetration of tine portion 430 at the selected site. The shorter length can help to prevent perforation through the wall of a structure, for example, the heart, at some implant locations, and can reduce a probability for penetrated tine portions 430 to interfere with blood vessels, which interference, for example, may compromise coronary blood supply, as will be described below in conjunction with FIG. 5.

Figure 2:
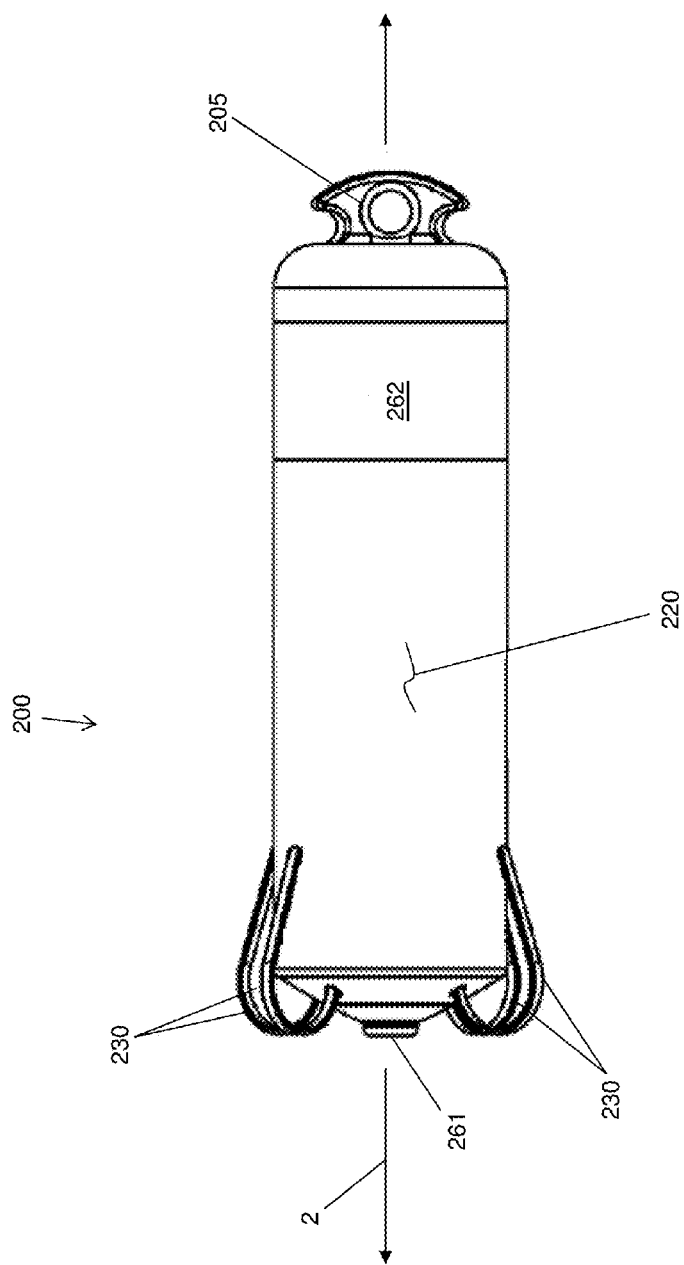
FIG. 2 is a plan view of an exemplary implantable medical device.
Figure 5:
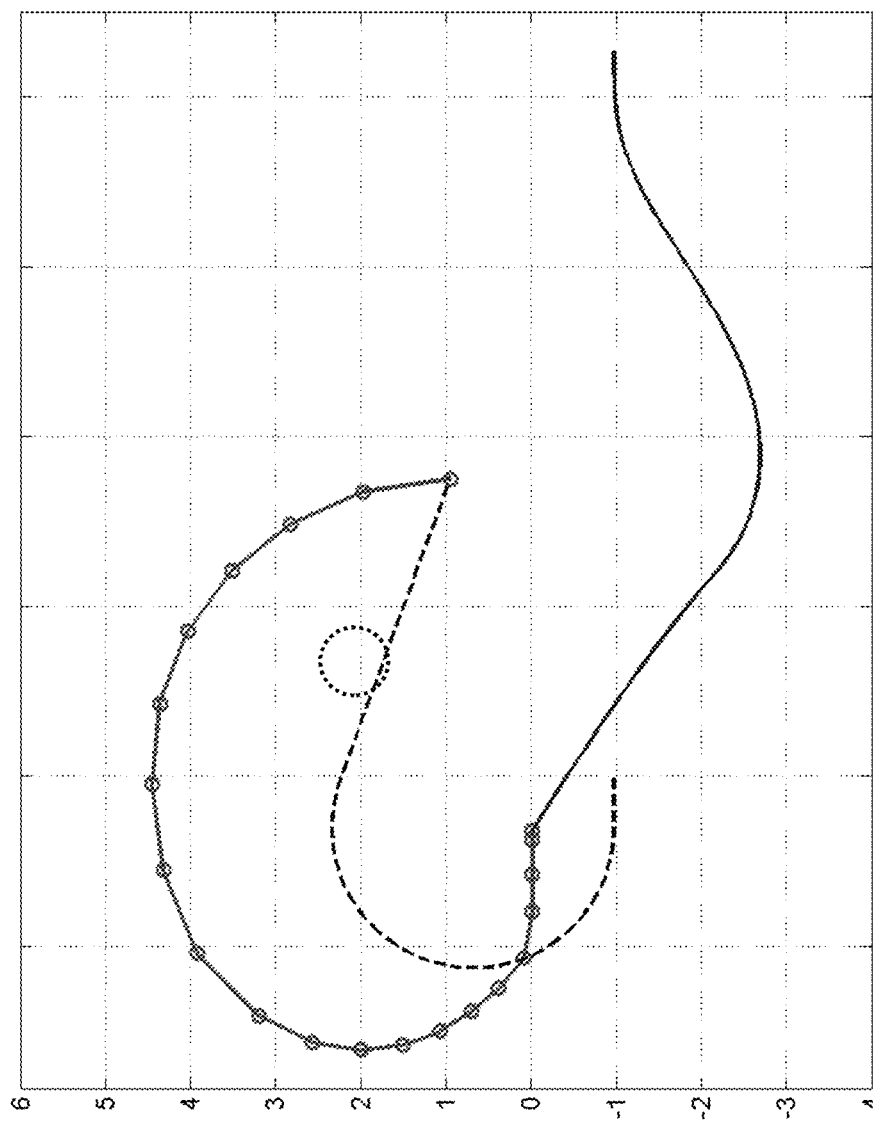
FIG. 5 is an estimated penetration path and an 'as set' relaxation plot for a tine portion of the exemplary device shown in FIG. 2.

FIG. 5 is an estimated tissue penetration path and an 'as set' relaxation plot for tine portion 230 of device 200 (FIG. 2), wherein tine portion 230 is formed from approximately 0.005 inch thick Nitinol. FIG. 5 includes a solid line, which represents the profile of tine portion 230 when device 200 is loaded in distal end 310 of catheter 300 (FIG. 3A) with hook segment 231 deformed to the open position. With reference back to FIGS. 3A-D, the origin, or zero coordinate, along the ordinate axis generally corresponds to the constraining wall of distal segment 310 of delivery catheter 300. The plot of FIG. 5 is made up of a segmented line connecting circles, which corresponds to the estimated penetration path of tine portion 230, for example, when device 200 is pushed out from distal end 310 and into tissue T (FIGS. 3B-D), and a dashed line, which represents the profile of tine portion 230, according to the pre-set curvature, toward which the penetrated tine portion 230 relaxes over time. The volume of tissue between the segmented line and the dashed line approaches that which is squeezed or compressed by the penetrated tine portion 230 as it relaxes over time; the greater this volume, the greater the probability for the penetrated tine to compress or pinch one or more blood vessels that perfuse the tissue. For example, the dotted line in FIG. 5 represents a potential coronary artery that may be compressed or pinched by tine portion 230. As alluded to above, the length of distal segment 232 is a factor contributing to the volume that is squeezed by penetrated tine portion 230, so that reducing the length of distal segment 232 may be desired. However, if the length of distal segment 232 is reduced, without modifying other aspects of tine portion 230, an orientation of tine portion 230 relative to tissue T, when hook segment 231 is in the open position, will be impacted such that tine portion 230 may be less likely to effectively penetrate into tissue T, for example, upon exiting through opening 313 of distal end 310 of catheter 300 (FIGS. 3A-B). Therefore, with reference to FIG. 4B, the tapering of hook segment 431 of tine portion 430 not only relieves strain but also allows for a more favorable orientation of the shorter distal segment 432 for tissue penetration (e.g., being directed along a line that is closer to normal to the tissue surface), when hook segment 431 is in the open position.

Various embodiments of tine portions for fixation of an implantable medical device, for example, as described below, incorporate a tapered hook segment and/or a shorter distal segment, to address the above described cyclic loading and/or potential tissue trauma. The following embodiments have been configured with reference to prior art tine portions of tissue-penetrating fixation components for medical devices, such as those described in the aforementioned commonly assigned United States Patent Application '690 (generally corresponding to tine portion 230), in order to allow a similar fit of devices, like device 200, within a delivery catheter, for example, having the tine portions deformed into the open position within distal portion 310 of catheter 300, and to maintain suitable baseline performance, for example, in terms of a deployment force (e.g., no greater than approximately 1-2 Newtons for a fixation component having four tine portions), an acute retraction force, for repositioning (e.g., between approximately 3-4 Newtons for a fixation component having four tine portions), atraumatic retraction, and an adequate acute fixation force (e.g., greater than approximately 2.5 Newtons for a fixation component having four tine portions).

FIG. 6A is a plan view of a medical device 600, according to some embodiments of the present invention. FIG. 6A illustrates device 600 including a hermetically sealed housing 620 and a pair of electrodes 661, 662; housing 620, like housing 220 of device 200, contains control electronics and a power source (not shown), which, for example, together with electrodes 661, 662, are adapted for cardiac pacing and sensing. FIG. 6A further illustrates device 600 including tine portions 630, which are adapted to penetrate tissue in order to secure device 600 at an implant site, for example, a cardiac site in the right atrium RA or the right ventricle RV (FIG. 1), having been deployed from distal end 310 of delivery catheter 300 (FIGS. 3A-D). According to some embodiments, tine portions 630 are included in a tissue-penetrating fixation component 63, which is shown, separate from device 600, in FIG. 6B.

FIG. 6B illustrates component 63 also including a base portion 603, from which tine portions 630 extend, preferably being integrally formed therewith, as described below. According to the illustrated embodiment, base portion 603 of fixation component 63 defines a longitudinal axis 6 of component 63 and is configured for attachment to device 600 so that axis 6 is approximately aligned with a longitudinal axis 20 of device 600. Component 63 may be part of a subassembly that forms a distal end of device 600, and which also includes electrode 661; such a subassembly is described in the aforementioned commonly-assigned United States Patent Application '690, in conjunction with FIGS. 3A-4B thereof, the description of which is hereby incorporated by reference. FIG. 6B further illustrates each tine portion 630 of tissue-penetrating component 63 including a hook segment 631 and a distal segment 632.

Figures 6C, 6D:
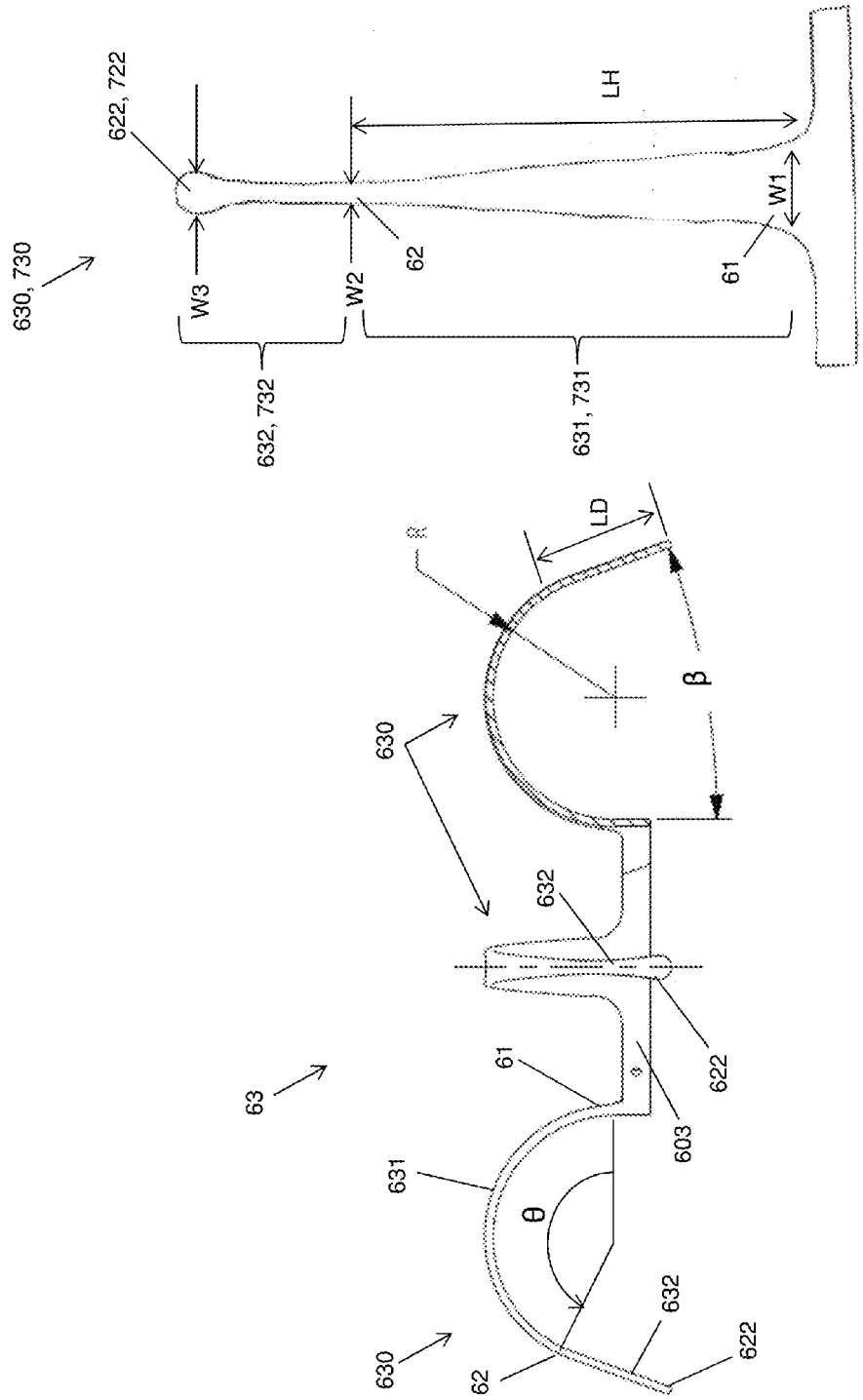
FIG. 6C is an elevation view of the component of FIG. 7B, according to some embodiments.
FIG. 6D is a plan view of a tine portion of the component of FIG. 7B, according to some embodiments.

With reference to FIG. 6C, which is an elevation view of component 63, each hook segment 631 extends along a pre-set curvature that encloses an angle δ, from a proximal end 61 thereof to a distal end 62 thereof. FIG. 6C illustrates each distal segment 632 extending along a relatively straight line that is approximately tangent to distal end 62 of hook segment 631. According to the illustrated embodiment, angle δ is less than 180 degrees, such that distal segment 632 extends away from axis 6. FIG. 6C further illustrates the preset curvature of hook segment 631 being defined by a single radius R. According to an exemplary embodiment, radius R is approximately 0.085 inch, an angle β, at which distal segment extends relative to axis 6, is approximately 20 degrees, and a length LD of distal segment 632 is between approximately 0.05 inch and approximately 0.1 inch.

According to some preferred embodiments, component 63 is manufactured by, first, laser cutting base portion 603 and tine portions 630, together, from a tube of superelastic and biocompatible metal (e.g., Nitinol), and then wrapping and holding each tine portion 630 about a mandrel for a heat setting process that pre-sets the illustrated curvature of each hook segment 631. Manufacturing methods such as these are known to those skilled in the art of forming Nitinol components. Although FIG. 6B shows base portion 603 of component 63 formed as a ring, wherein tine portions 630 are integrally formed therewith and spaced apart from one another about a perimeter of the ring, in alternate embodiments of tissue penetrating fixation components, one or more tine portions may be formed individually and then attached to a base portion that is configured in any suitable fashion for attachment to device 600.

FIG. 6D is a plan view of one of tine portions 630, prior to forming the pre-set curvature thereof, in which the above-described tapering for strain relief along hook segment 631, from first width W1 to smaller, second width W2 may be seen. When, for example, in the aforementioned exemplary embodiment, component 63 is manufactured from Nitinol tubing that has a thickness of approximately 0.005 inch, and hook segment 631 thereof has a length LH of approximately 0.23 inch, first width W1 may be between approximately two to five times greater than second width W2 to provide strain relief for improved fatigue life. Yet, if the smaller, second width W2, for example, being approximately 0.010 inch, were to define an entirety of distal segment 632, distal segment 632 may tear tissue upon retraction therefrom, for example, when repositioning device 600. So, with further reference to FIG. 6D, distal segment 632 of tine portion 630 is terminated by a tissue-piercing tip 622 that has a width W3, which is greater than second width W2, for example, approximately two to three times greater, in order to be atraumatic to tissue. In the aforementioned exemplary embodiment, first width W1 is between approximately 0.034 inch and approximately 0.05 inch, second width W2 is approximately 0.010 inch, and third width W3 is approximately 0.02 inch.

Figure 7A:
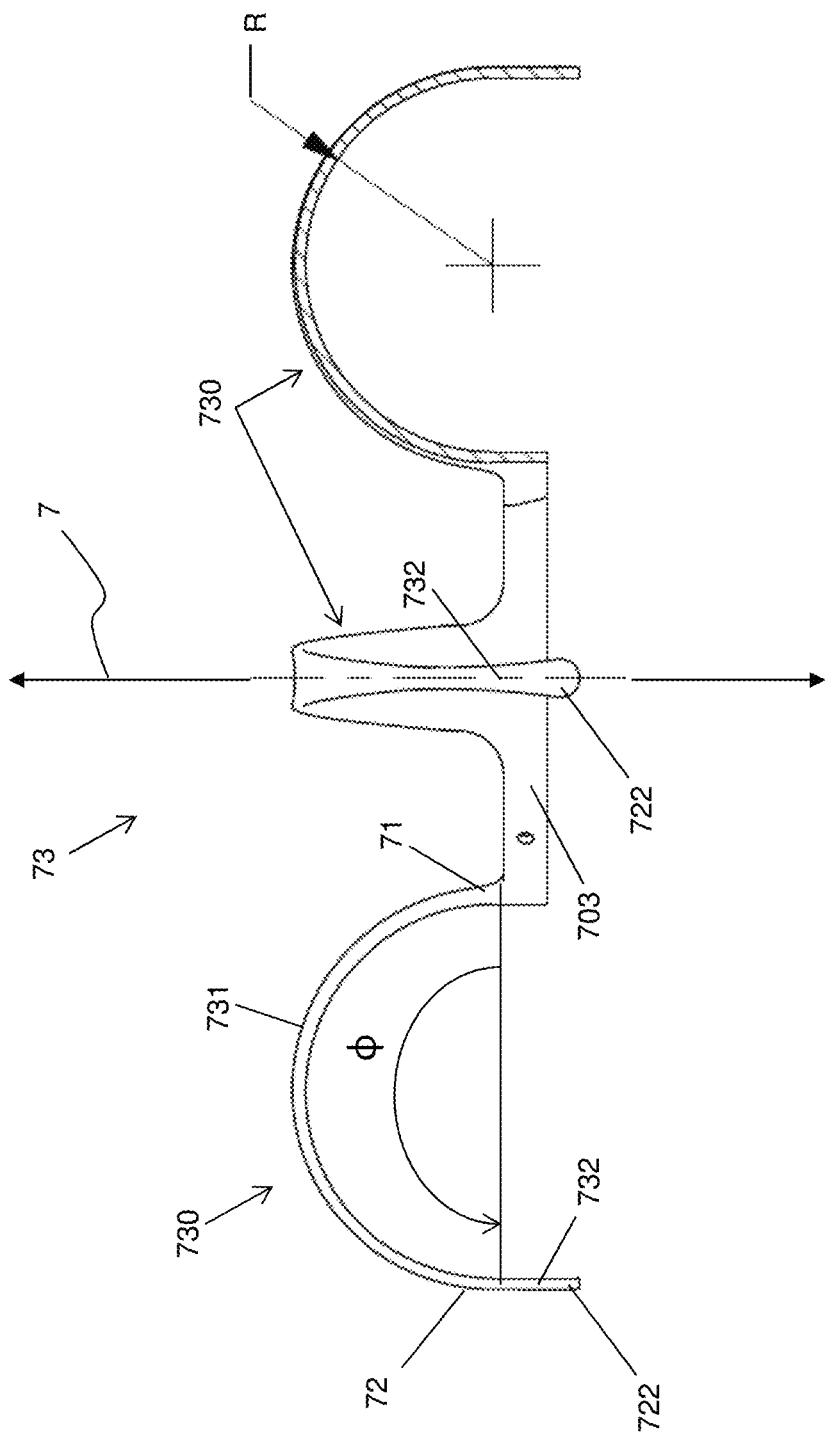
FIG. 7A is an elevation view of a tissue-penetrating fixation component, according to some alternate embodiments, which may be incorporated in the device of FIG. 6A.

FIG. 7A is an elevation view of a tissue-penetrating fixation component 73, according to some alternate embodiments of the present invention, which may be incorporated in device 600 as an alternative to component 63, such that a longitudinal axis 7 of component 73 is approximately aligned with longitudinal axis 20 of device 600. FIG. 7A illustrates component 73 including a base portion 703, similar to base portion 603 of component 63, and a plurality of tine portions 730, each of which includes a hook segment 731 and a distal segment 732. Tine portions 730 and base portion 703 are preferably integrally formed according to the method described above for component 63. Furthermore, each tine portion 730, prior to the pre-setting of a curvature of hook segment 731, may be configured like tine portion 630 as described above in conjunction with FIG. 6D, wherein the aforementioned exemplary values for widths W1, W2, W3, thickness t and lengths LD, LH are suitable. However, with further reference to FIG. 7A, the pre-set curvature along which hook segment 731 extends, from a first end 71 thereof and a second end 72 thereof, encloses an angle φ, which is 180 degrees, so that distal segment 732 extends, between a tissue-piercing tip 722 thereof and second end 72 of hook segment 731, along a line that is approximately parallel to axis 7. The pre-set curvature of hook segment 731, like hook segment 631, is defined by a single radius R, which may be approximately 0.085 inch.

Figure 7B:
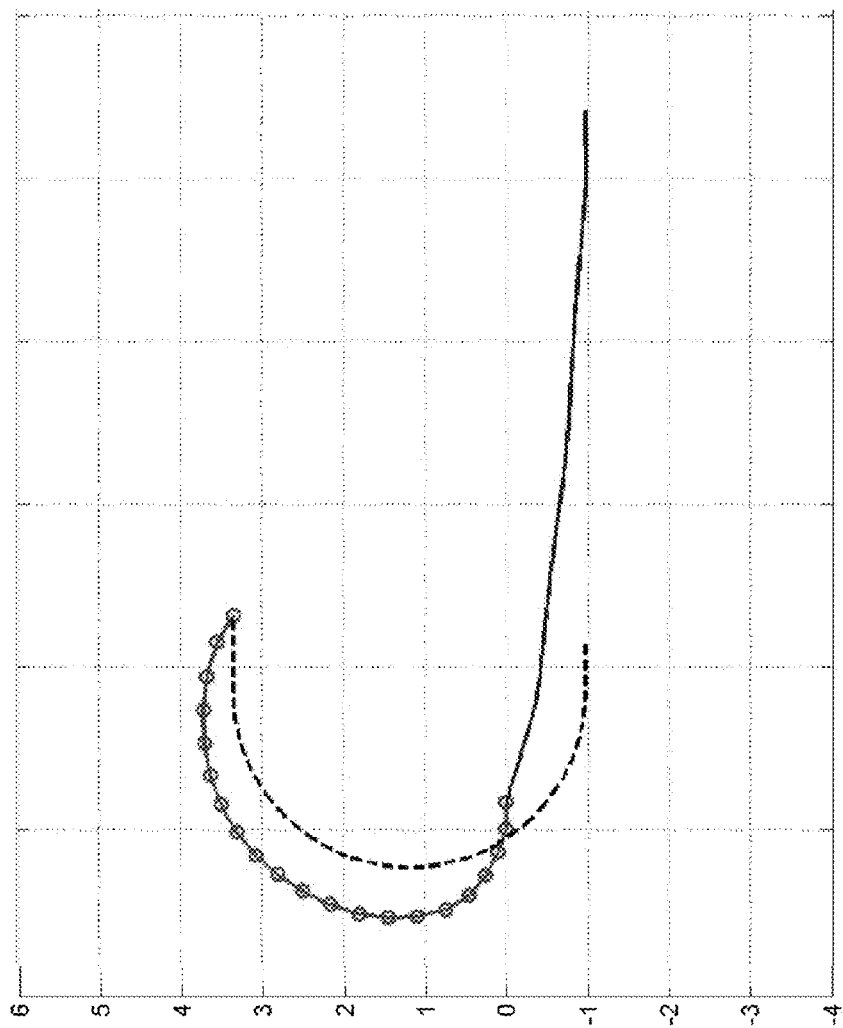
FIG. 7B is an estimated penetration path and an 'as set' relaxation plot for a tine portion of the component shown in FIG. 7A.

FIG. 7B is an estimated penetration path and an 'as set' relaxation plot for tine portion 730 of component 73, which may be compared to that of tine portion 230 (FIG. 5). FIG. 7B illustrates, with a solid line, tine portion 730 having been elastically deformed into the open position, for example, as would be the case when device 600 includes component 73 and is loaded within a delivery catheter, for example, distal end 310 of delivery catheter 300 (FIG. 3A). In comparing the solid lines of FIGS. 5 and 7B, it may be appreciated how the strain relief of tapering flattens the deformed profile of tine portion 730 relative to that of tine portion 230, and that the open position of tine portion 730 orients distal segment 732 of tine portion 730 along a line that is nearly normal to the ordinate axis, which generally corresponds to the above-described tissue surface, for effective tissue penetration. Furthermore, in comparing the estimated tissue penetration path of tine portions 230 and 730 (segmented lines connecting the circles), relative to the corresponding relaxed profiles (dashed lines), it can be seen that, due to the shorter length and more open pre-set curvature, tine portion 730 does not encompass as large a volume of tissue, relative to the pre-set curvature, toward which the penetrated tine portion 730 relaxes over time, upon full penetration, so that the above described risk of perforation and/or pinching of blood vessels is reduced.

Figure 8B:
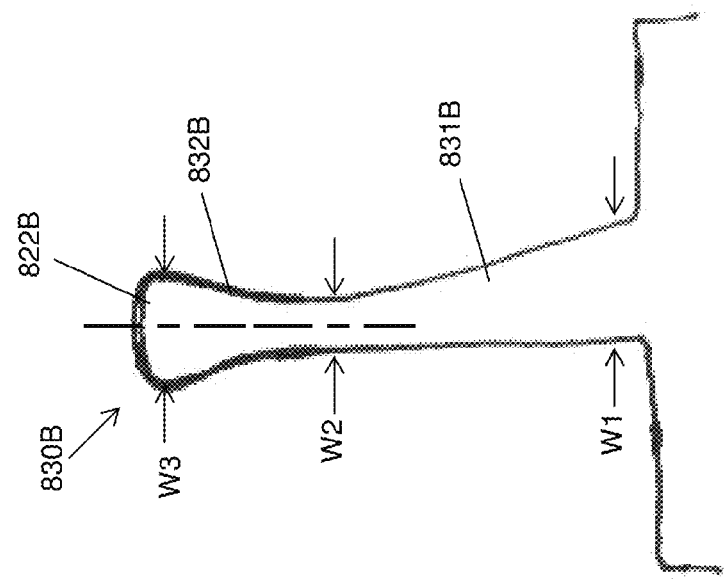
FIGS. 8A-B are plan views of tine portions, according to some alternate embodiments.
Figure 8A:
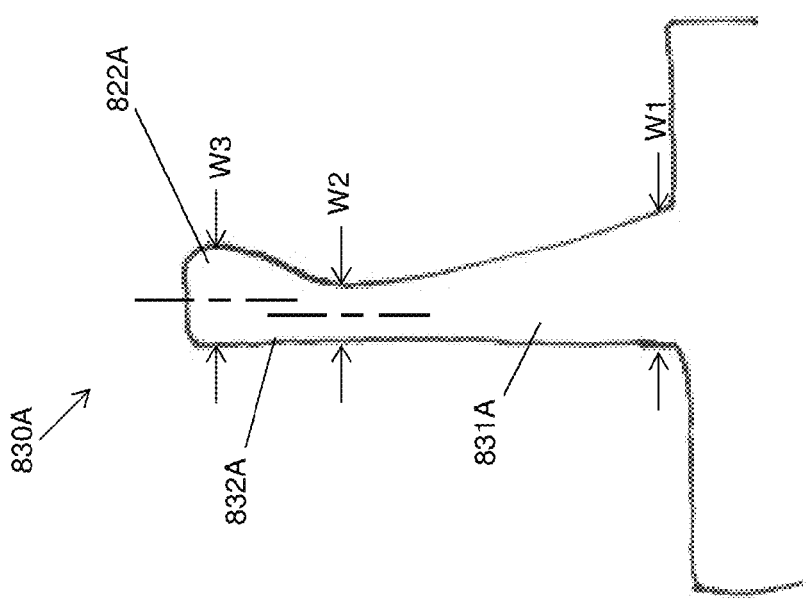

FIGS. 8A-B are plan views of tine portions 830A, 830B, prior to pre-setting a curvature thereof, according to some alternate embodiments, either of which may be formed in component 63, 73 in lieu of tine portions 630, 730, for example, to increase the ease of tolerance control and inspection. FIGS. 8A-B illustrate hook segments 831A, 831B of tine portions 830A, 830B having a single-sided, or asymmetric taper. According to the illustrated embodiments, widths W1, W2, and W3 are designated at generally the same locations along hook segments 831A, 831B and distal segments 832A, 832B, as previously described for tine portions 630 and 730. Furthermore, it should be understood that, according to some preferred embodiments, a thickness of each tine portion 830A, 830B (into the page), for example, approximately 0.005 inch, is approximately constant along an entire length of each tine portion 830A, 830B, since components that would include tine portions 830A, 830B are preferably formed from a Nitinol tube according to the method described above. FIG. 8A further illustrates distal segment 832A of tine portion 830A being terminated in a tissue-piercing tip 822, at which width W3 has a center line that is offset from a center line of second width W2; while FIG. 8B illustrates a tissue-piercing tip 822B of distal segment 832B, at which width W3 has a center line approximately aligned with that of second width W2. According to some exemplary embodiments, first width W1 is between approximately 0.034 inch and approximately 0.05 inch, second width W2 is approximately 0.010 inch, and third width W3 is approximately 0.02 inch.

FIGS. 9A-D are profiles and corresponding estimated penetration path and 'as set' relaxation plots of various tine portions 930A, 930B, 930C, 930D, according to yet further embodiments of the present invention, wherein the profiles, per the pre-set curvatures of hook segments 931A-D, accommodate for a relatively shorter length of distal segments 932A-D thereof, for example, compared to that of tine portion 230 (FIG. 5). FIGS. 9A-D illustrate the pre-set curvature of each hook segment 931A-D being defined by two radii, R1 and R2, wherein R2 is greater than R1. According to exemplary embodiments of tine portions 930A, 930B, radius R1 is approximately 1.04 mm and radius R2 is approximately 1.65 mm, while in an exemplary embodiment of tine portion 930C, radius R1 is approximately 0.5 mm and radius R2 is approximately 1.65 mm, and, in an exemplary embodiment of tine portion 930D, radius R1 is 0.25 mm and radius R2 is approximately 2.4 mm. It should be noted that none of tine portions 930A-D, as depicted in the corresponding plots, include tapering along the corresponding hook segments 931A-D thereof. Yet, it is contemplated that a tapering of hook segments 931A-D, for example, similar to that described above, will provide strain relief for improved fatigue life and allow for shorter tine portions 930A-D without compromising the orientation of distal segments 932A-D, when hook segments 931A-D are deformed into the open position.

Each of tine portions 930A-D may be one of a plurality, which are included in a tissue-penetrating component, and that extend from a base portion 903 of the component, wherein base portion 903 defines an axis 9 of the component, and may be similar to the above described base portions 603, 703 of components 63, 73. FIGS. 9A-D further illustrate each of tine portions 930A-D including a proximal segment 933A-D that extends between base portion 903 and the corresponding hook portion 931A-D. Each of proximal segments 933A, 933B is shown extending approximately parallel to axis 9, while each of proximal segments 933C, 933D is shown extending from base portion 903 toward axis 9, for example, to increase an overall arc length of each of tine portions 930C, 930D for added flexibility during retraction into catheter distal end 310 (FIGS. 3A-C), when the corresponding hook segment 931C, 931D is being elastically deformed to the open position (solid line of plots). Furthermore, although the orientation of distal segments 932C, 932D, when tine portions 930C, 930D are in the open position, is less favorable for ease of tissue penetration that that of other embodiments, the extension of proximal segments 933C, 933D toward axis 9 can contribute to a reduction in compressed tissue volume without a tapering of hook segments 931C, 931D.

Figure 9A:
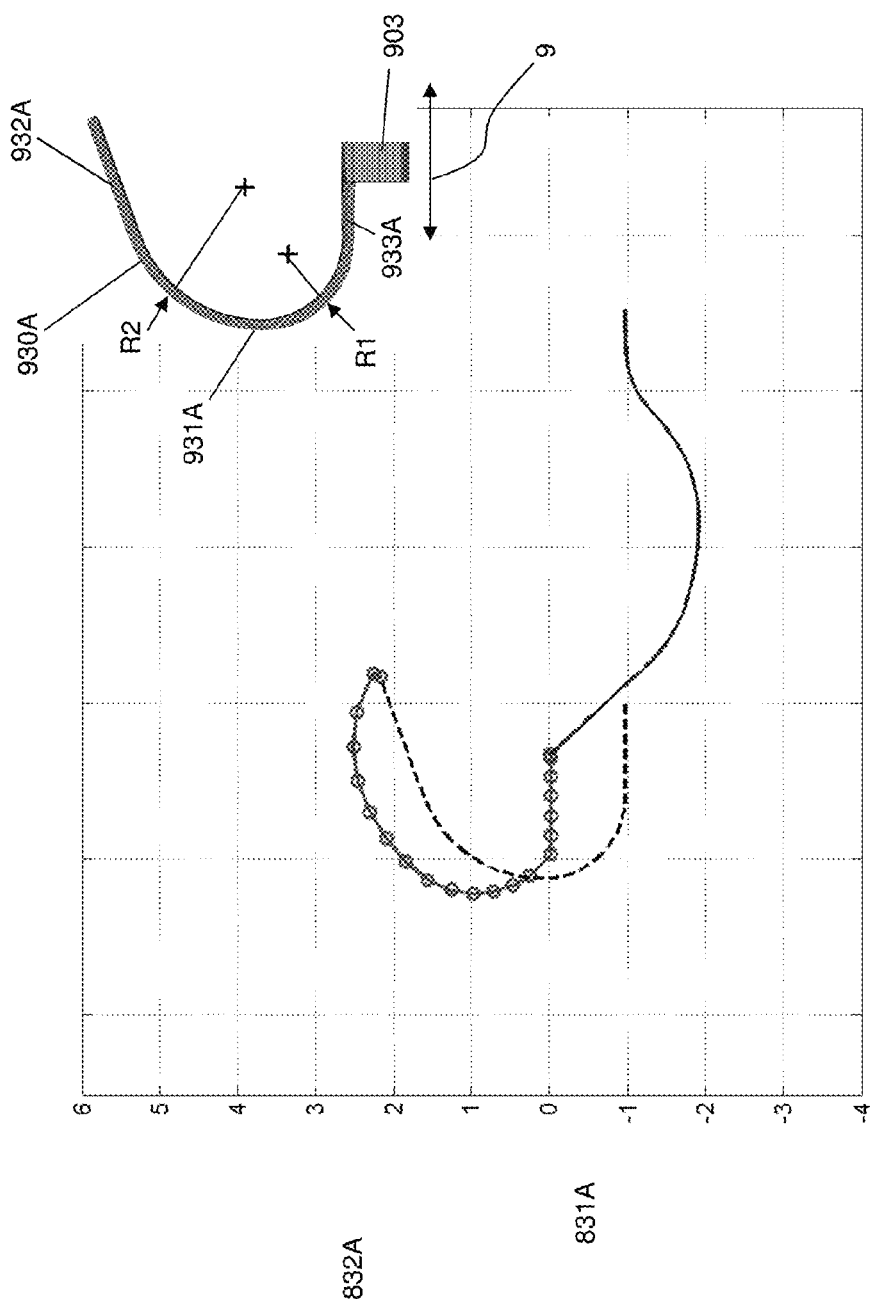
FIGS. 9A-D are profiles and corresponding estimated penetration path and 'as set' relaxation plots of various tine portions, according to additional embodiments.
Figure 9B:
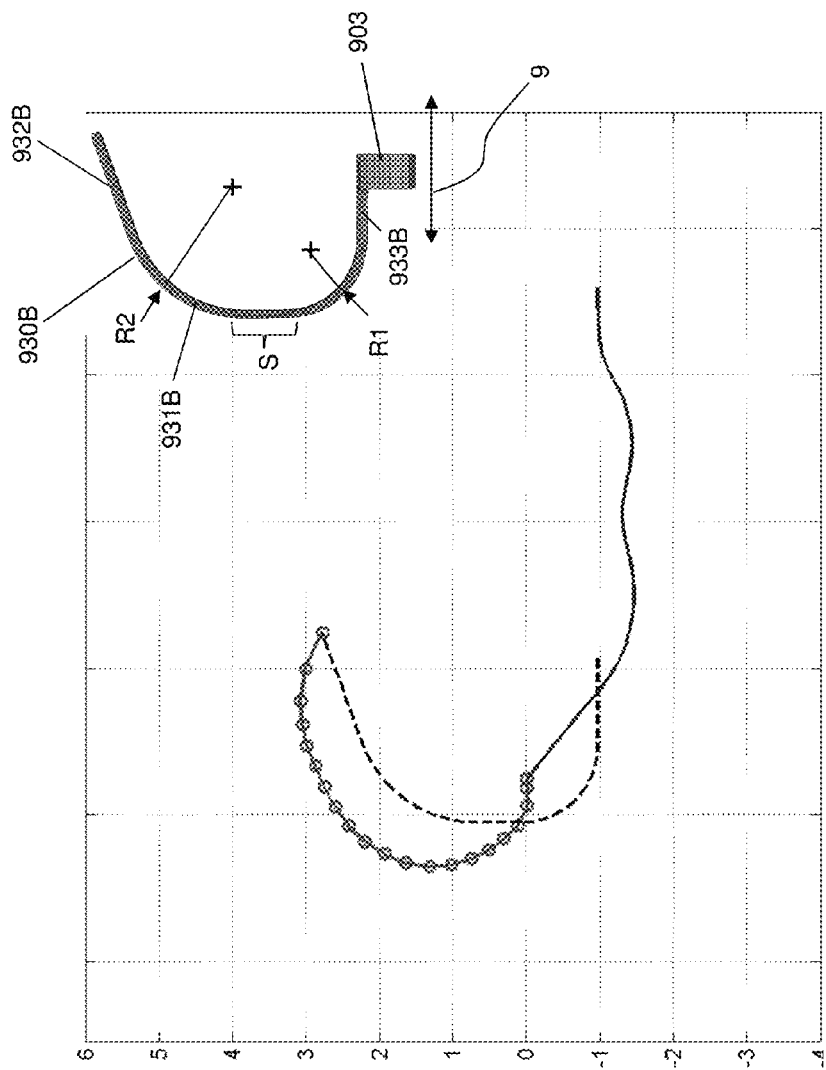
Figure 9C:
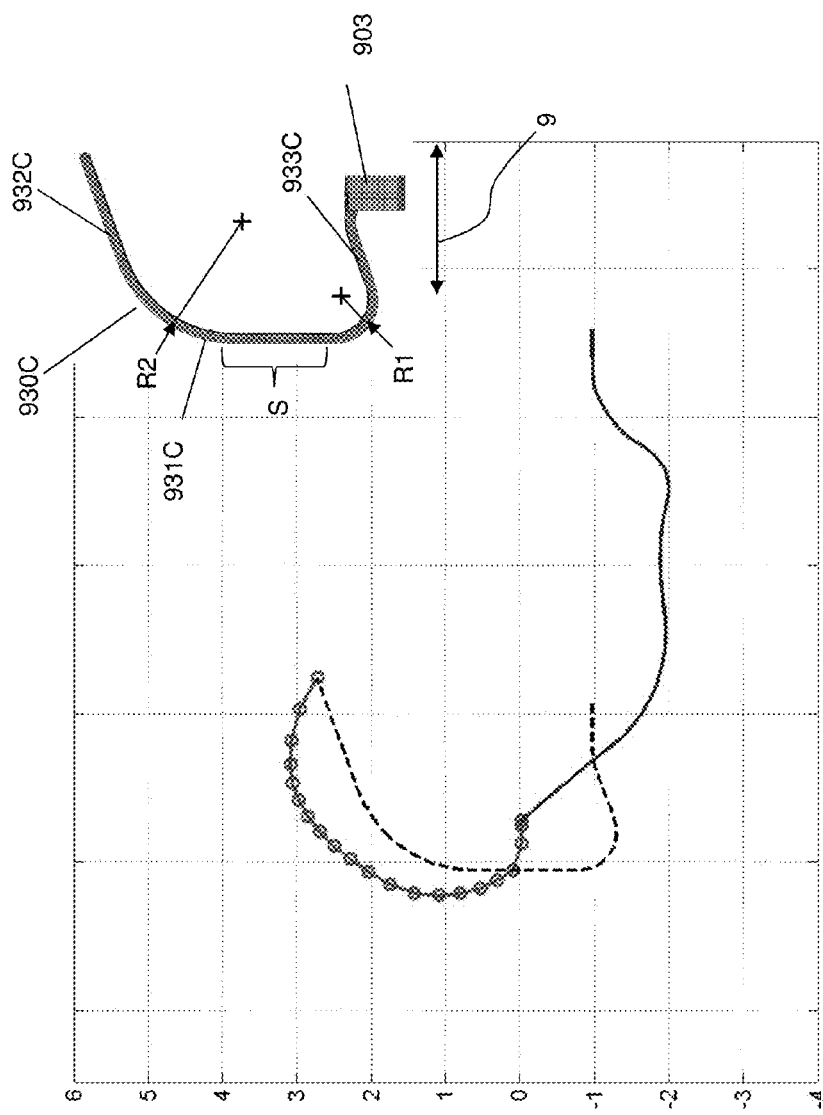
Figure 9D:
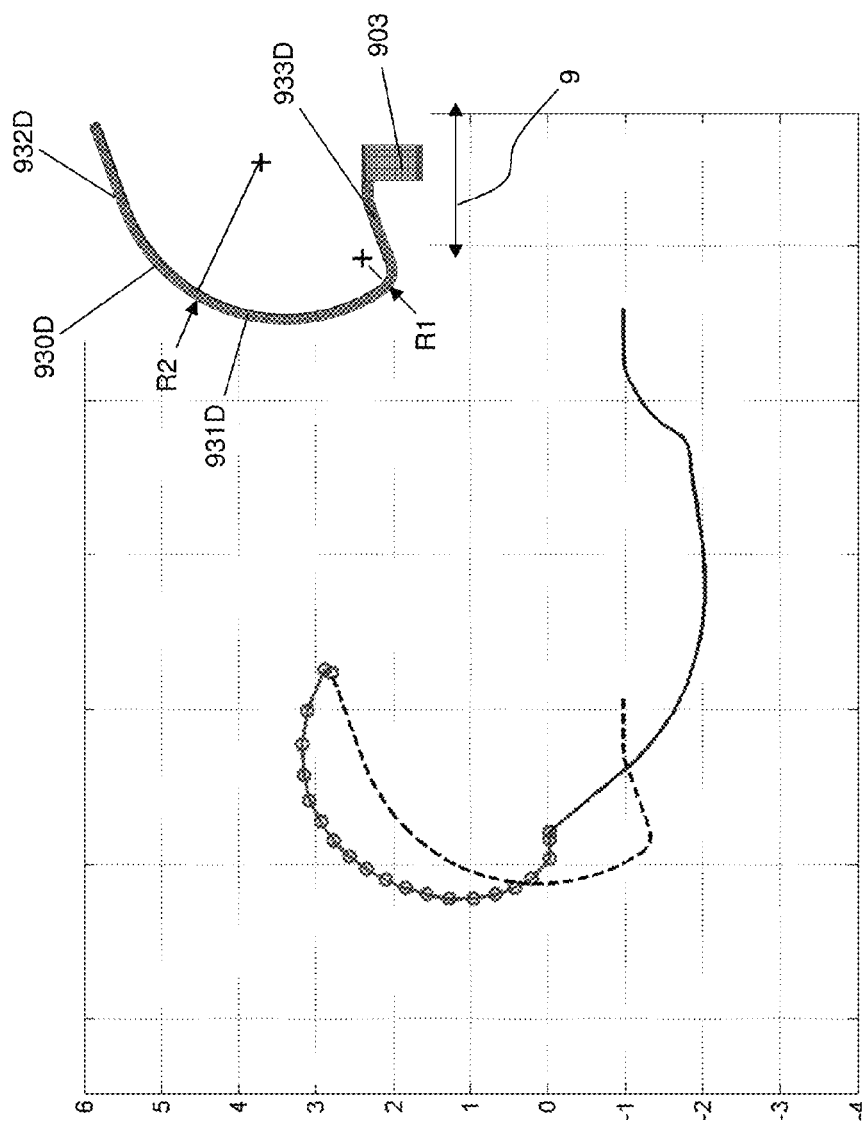

With further reference to FIGS. 9B-C, each hook portion 931B, 931C is also defined by a straight section S that extends between radii R1, R2. With further reference to the solid lines in the plots of FIGS. 9A-D, it may be seen how straight sections S can somewhat flatten the opened profile of tine portions 930B, 930C. Finally, in comparing the segmented lines of the FIG. 9A-D plots, which correspond to the estimated tissue penetration path of each of tine portions 930A-D, to that in the FIG. 5 plot for tine portion 230, it can be appreciated that the relatively shorter lengths of distal segments 932A-D, in combination with the corresponding profiles of tine portions 930A-D, lead to a reduction in tissue volume that is potentially compressed by each of the penetrated tine portions 930A-D during subsequent relaxation toward the pre-set curvature (dashed lines).

Because a reduction in the length, and/or tapering for strain relief of tine portions, can, in some instances, hinder initial tine penetration upon deployment (e.g., according to the method described above in conjunction with FIGS. 3B-C) additional embodiments of the present invention, which are described below in conjunction with FIGS. 10A-C and FIGS. 11A-B, include tissue-piercing distal tips that are configured to enhance initial tine penetration. With reference to FIGS. 3A-B, the initial penetration of tine portions 230 rely upon a stiffness of tine portions 230 being greater than that of tissue T, and upon an orientation of tissue-piercing tip 322 relative to tissue T, when device 200 is loaded in catheter distal end 310, with hook segments 31 elastically deformed into the open position.

Figure 1:
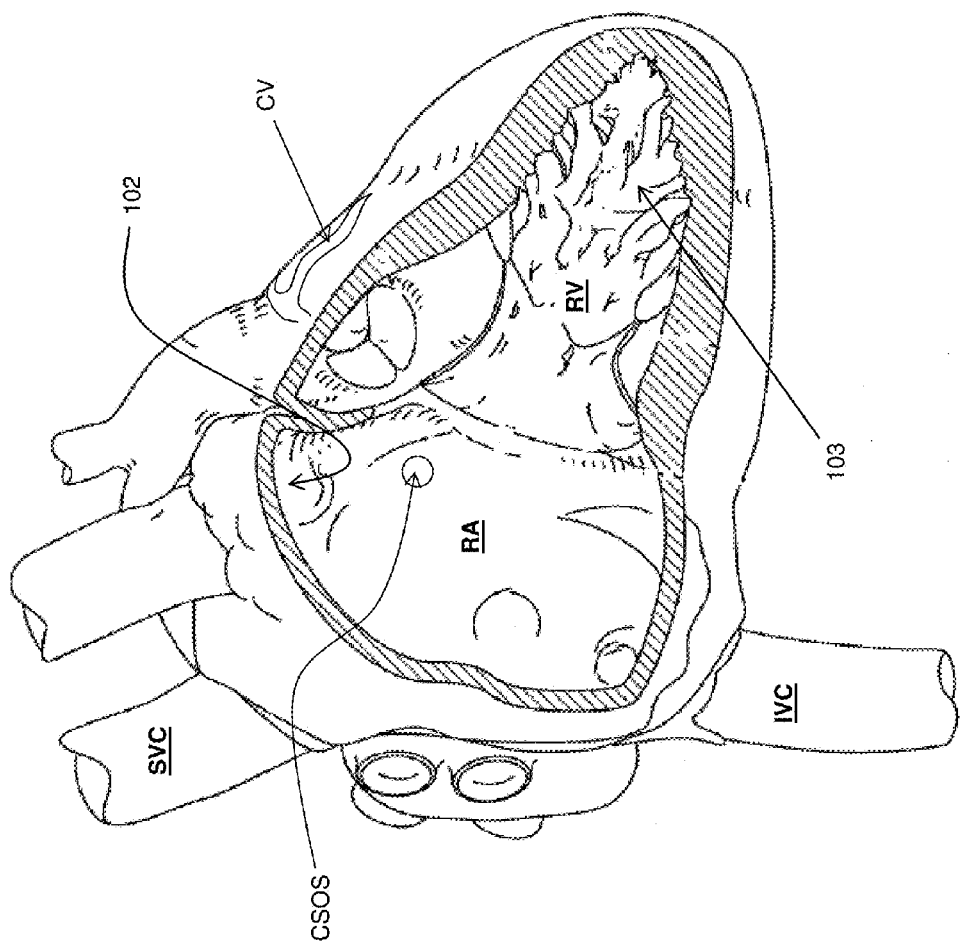
FIG. 1 is a schematic diagram showing potential implant sites for embodiments of the present invention.

FIG. 10A is a plan view of an implantable medical device 500, according to some embodiments of the present invention. FIG. 10A illustrates device 500 including a hermitically sealed housing 520 and a pair of electrodes 561, 562; housing 520, like housing 220 of device 200, contains control electronics and a power source (not shown), which, for example, together with electrodes 561, 562, are adapted for cardiac pacing and sensing. FIG. 10A further illustrates device 500 including tine portions 530, which are adapted to penetrate tissue in order to secure device 500 at an implant site, for example, a cardiac site in the right atrium RA or the right ventricle RV (FIG. 1).

FIG. 10B is a perspective view of a tissue-penetrating fixation component 53, according to some embodiments of the present invention, which is shown separated from device 500, and which includes tine portions 530. FIG. 10B illustrates component 53 also including a base portion 503, from which tine portions 530 extend. According to the illustrated embodiment, base portion 503 of fixation component 53 defines a longitudinal axis 5 of component 53 and is configured for attachment to device 500 so that axis 5 is approximately aligned with a longitudinal axis 25 of device 500. Component 53 may be part of a subassembly that forms a distal end of device 500, and which also includes electrode 561, for example, like the aforementioned subassembly that is disclosed in the above referenced and incorporated by reference passages of the detailed description of commonly-assigned United States Patent Application '690.

FIG. 10B further illustrates each tine portion 530 of tissue-penetrating fixation component 53 including a hook segment 531 and a distal segment 532. Each hook segment 531 is shown extending along a curvature that encloses an angle ψ, from a proximal end 51 thereof to a distal end 52 thereof; and each distal segment 532 is shown extending along a relatively straight line that is approximately tangent to distal end 52 of hook segment 531. Each distal segment 532 is shown extending toward axis 5, and, according to an exemplary embodiment, angle ψ is approximately 200 degrees. According to some preferred embodiments, component 53 is manufactured by, first, laser cutting base portion 503 and tine portions 530, together, from a tube of superelastic and biocompatible metal (e.g., Nitinol), and then wrapping and holding each tine portion 530 about a mandrel for a heat setting process that presets the illustrated curvature of each hook segment 531. As mentioned above, manufacturing methods such as these are known to those skilled in the art of forming Nitinol components. Although FIG. 10B shows base portion 503 of component 53 formed as a ring, wherein tine portions 530 are integrally formed therewith, and spaced apart from one another about a perimeter of the ring, in alternate embodiments of tissue penetrating fixation components, one or more tine portions may be formed individually and then attached to a base portion that is configured in any suitable fashion for attachment to device 500.

In order to provide more flexibility in selecting a suitable implant location for device 500, a length of distal segment 632 of each tine portion 630 is relatively short compared to that of distal segment 232 of tine portion 230, for example, between approximately 0.05 inch and approximately 0.1 inch. The shorter length can help to prevent perforation through the wall of a structure, for example, the heart, at some implant locations, and can reduce a probability for penetrated tine portions 530 to interfere with blood vessels, which interference, for example, may compromise coronary blood supply, as described above. However, with reference back to FIGS. 3A-C, after device 500 is loaded in distal end 310 of catheter 300, and opening 313 of distal end 310 is positioned in proximity to tissue at a potential implant site, the reduced length of tine portions 530 may hinder initial tine penetration. A sharper terminal end of distal segment 532 can solve this problem but may lead to tissue tearing, upon insertion and/or retraction; thus a relatively blunt terminal end of distal segment 532 is preferred. So, with further reference to FIG. 10B, each distal segment 532 includes a tooth 520 and a relatively blunt end 540, which surrounds tooth 520.

FIG. 10B illustrates end 540 including a pair of legs 541 and a distal arch 542 that extends between legs 541, distal to tip 522 of tooth 520, for example, being spaced apart therefrom by approximately 0.005 inch. Each tooth 520 has a length, which is defined from a foot 521 thereof to a tissue-piercing tip 522 thereof, for example, being between approximately 0.025 inch and approximately 0.045 inch, and legs 541 extend along the length of tooth 520, on opposing sides thereof. Each tooth 520 and corresponding end 540 may be laser cut at the same time that tine portions 530 and base portion 503 are cut from the aforementioned tube.

Figure 10C:
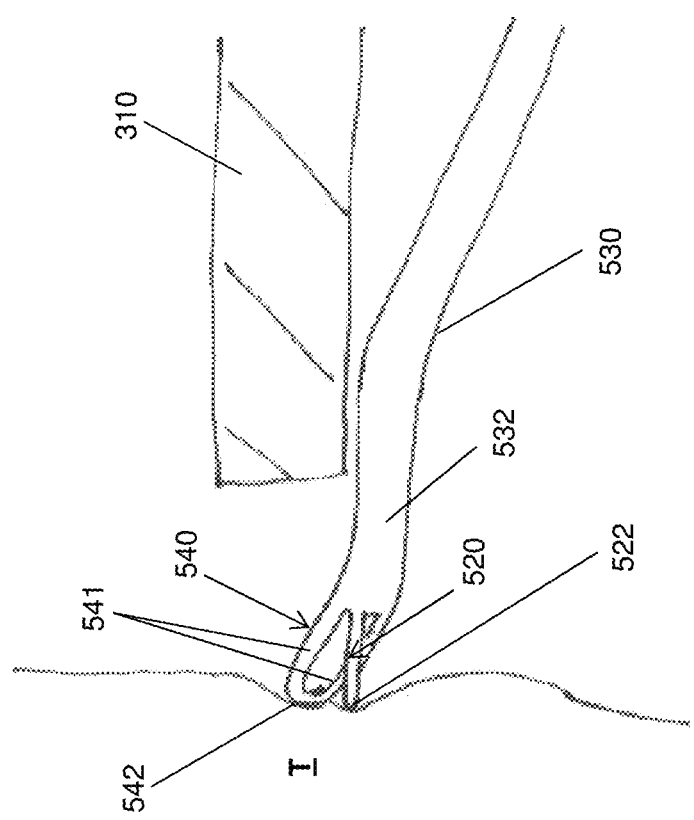
FIG. 10C is an enlarged detail view of a distal segment of one of the tine portions of the FIG. 10B component initially contacting tissue at an implant site.

According to the illustrated embodiment, legs 541 of end 540 are configured to bend in elastic deformation when distal arch 542 is pushed against tissue at a potential implant site, for example, as illustrated in FIG. 10C, so that tip 522 of tooth 520, which is configured to resist bending, is exposed to pierce the tissue. FIG. 10C is an enlarged detail view of distal segment 532 as tine portion 530 is pushed into contact with tissue T at the implant site. With reference back to FIGS. 3A-B, it should be understood that pushing distal arch 542 against the tissue T may be accomplished, as described above for device 200, after device 500 is loaded into distal end 310 of catheter 300 so that hook segments 531 of tine portions 530 are elastically deformed into the open position, at which distal segments 532 are directed distally toward opening 313 of distal end 310. After tip 522 of each tooth 520 has pierced the tissue, in response to the relatively high push force for initial deployment, legs 541 of end 540 can relax back into line with tooth 520 so that distal arch 542, upon subsequent penetration/insertion of tine portions 530 into tissue, and upon retraction thereof from the tissue, if necessary, prevents tip 522 from tearing the tissue. With reference back to FIG. 10B, according to an exemplary embodiment, a thickness t of each tine portion 530, which is relatively constant along the entire length thereof, is approximately 0.005 inch, a width wf of foot 521 of tooth 520 is between approximately 0.010 inch and approximately 0.015 inch, a width wt of tip 522 of tooth 520 is approximately 0.003 inch, and a width we of legs 541 and distal arch 542 is approximately 0.005 inch.

FIG. 11A is an elevation view of a tissue-penetrating fixation component 83, according to some alternate embodiments of the present invention, which may also be incorporated in the exemplary device of FIG. 10A. FIG. 11A illustrates component 83 including a base portion 803 and a plurality of tine portions 830 extending therefrom, similar to component 53, wherein each tine portion 830 includes a hook segment 831 and a distal segment 832 that are configured to address both of the aforementioned issues related to tissue penetration and fatigue life. Component 83 may be cut and formed from a Nitinol tube in a manner similar to that described above for component 53. FIG. 10A further illustrates each hook segment 831 being pre-set to extend along a curvature that encloses angle $\phi$, from a proximal end 81 thereof to a distal end 82 thereof; and each distal segment 832 is shown extending along a relatively straight line that is approximately tangent to distal end 82 of hook segment 831. According to the illustrated embodiment, angle $\phi$ is approximately 180 degrees, so that each distal segment 832 extends approximately parallel to a longitudinal axis 8 of component 83. The pre-set curvature of hook segment 831 is defined by a single radius R, which may be approximately 0.085 inch.

FIG. 11B is a plan view of tine portion 830, prior to forming the pre-set curvature thereof. FIGS. 11A-B illustrate each tine portion 830 including a tapered hook portion 831, similar to hook portions 631, 731 of tine portions 630, 730, described above, wherein second width W2, in proximity to distal end 82 of hook segment 831, is less than first width W1, in proximity to a proximal end 81 of hook segment 831. FIGS. 11A-B further illustrate distal segment 832 having a width W3 that is greater than the second width W2. Distal segment 832, like distal segment 532 of component 53, includes tooth 520 and end 540 to facilitate tissue piercing without tearing, as described above. Like component 53, a thickness t of each tine portion 830, which is relatively constant along the entire length thereof, may be approximately 0.005 inch, and distal segment 832 thereof may conform to the aforementioned exemplary dimensions of tooth 520 and end 540.

In the foregoing detailed description, the invention has been described with reference to specific embodiments. However, it may be appreciated that various modifications and changes can be made without departing from the scope of the invention as set forth in the appended claims.

The invention claimed is:

1. A tissue-penetrating fixation component for an implantable medical device, the component comprising a base portion and at least one tine portion, the base portion defining a longitudinal axis of the component and being configured for attachment to the medical device so that the longitudinal axis of the component extends parallel to a longitudinal axis of the device, the at least one tine portion comprising a hook segment and a distal segment, the hook segment being pre-set to extend along a curvature that encloses an angle of between 135 degrees and 270 degrees, from a proximal end thereof, in proximity to the base portion, to a distal end thereof, the distal segment being pre-set to extend from the distal end of the hook segment along a relatively straight line that is tangent to the distal end of the hook segment, and the hook segment being elastically deformable from the pre-set curvature to an open position; and wherein:

the distal segment comprises a tooth and an end that surrounds the tooth;

the tooth includes a foot and a tissue-piercing tip, a length of the tooth being defined from the foot to the tip;

the end includes a pair of legs and a distal arch, the legs extending along the length of the tooth, on opposing sides thereof, the distal arch extending between the legs and distal to the tip, the legs being configured to bend in elastic deformation, when the hook segment is elastically deformed to the open position and a force is applied, along the longitudinal axis of the component, to push the distal arch of the distal segment against tissue, for initial tissue penetration, and the bending of the legs exposing the tip of the tooth to the tissue; and the tooth is configured to resist bending when the force is applied.

2. The component of claim 1, wherein the tooth of the distal segment of the at least one tine portion tapers from a first width thereof, at the foot, to a smaller, second width thereof, at the tip.

3. The component of claim 2, wherein the length of the tooth of the distal segment is between 0.03 inch and 0.05 inch.

4. The component of claim 2, wherein the first width is between 0.010 inch and 0.015 inch, and the second width is 0.003 inch.

5. The component of claim 1, wherein the hook segment of the at least one tine portion tapers from a first width thereof, at the proximal end thereof, to a smaller, second width thereof, in proximity to the distal end thereof.

6. The component of claim 5, wherein a width of the distal segment of the at least one tine portion, defined by the pair of legs thereof, is greater than the second width of the hook segment.

7. The component of claim 1, wherein the distal segment of the at least one tine portion extends toward the longitudinal axis, when the hook segment of the at least one tine portion conforms to the pre-set curvature.

8. The component of claim 1, wherein the distal segment of the at least one tine portion extends parallel to the longitudinal axis, when the hook segment of the at least one tine portion conforms to the pre-set curvature.

9. The component of claim 1, wherein the preset curvature of the hook segment of the at least one tine portion is defined by a single radius, the radius being 0.085 inch, and a length of the distal segment is between 0.05 inch and 0.1 inch.

10. The component of claim 1, wherein:

the base portion comprises a ring that extends around the longitudinal axis; and the at least one tine comprises a plurality of tines spaced apart from one another around a circumference of the ring.

11. The component of claim 1, wherein the at least one tine portion has a substantially constant thickness along an entire length thereof, from the proximal end of the hook segment to the distal arch of the end of the distal segment.

* * * * *